United States Patent
Hiwatashi et al.

(10) Patent No.: US 6,375,932 B1
(45) Date of Patent: *Apr. 23, 2002

(54) HAIR COSMETIC COMPOSITION CONTAINING AMINE-OXIDE POLYMER

(75) Inventors: Tomoaki Hiwatashi; Yasuo Kitani; Kanji Narazaki; Kayo Itou; Kazuhide Hayama, all of Mie (JP)

(73) Assignee: Mitsubishi Chemical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/925,669

(22) Filed: Sep. 9, 1997

(30) Foreign Application Priority Data

| Sep. 10, 1996 | (JP) | ............................................. 8-239406 |
| Sep. 10, 1996 | (JP) | ............................................. 8-239409 |
| Sep. 17, 1996 | (JP) | ............................................. 8-244910 |
| Sep. 18, 1996 | (JP) | ............................................. 8-246055 |

(51) Int. Cl.[7] ............................................. A61K 7/035
(52) U.S. Cl. ..................... 424/47; 424/45; 424/DIG. 1; 424/DIG. 2; 424/70.11; 424/70.13; 424/70.19; 424/70.21; 424/70.28; 424/70.31; 514/880; 514/944; 514/945
(58) Field of Search ....................... 424/45, 47, DIG. 1, 424/DIG. 2, 70.11, 70.13, 70.19, 70.21, 70.28, 70.31; 514/957, 944, 945, 880; 510/119, 121

(56) References Cited

U.S. PATENT DOCUMENTS

| 3,313,734 | A | * | 4/1967 | Lang et al. |
| 4,013,787 | A | | 3/1977 | Varlerberghe et al. |
| 4,897,262 | A | * | 1/1990 | Nandagiri et al. ........ 424/70.11 |
| 5,021,238 | A | * | 6/1991 | Martino et al. ......... 424/DIG. 2 |
| 5,094,838 | A | * | 3/1992 | Benson et al. ......... 424/DIG. 1 |
| 5,126,126 | A | * | 6/1992 | Varaprath et al. .............. 424/47 |
| 5,176,898 | A | * | 1/1993 | Goldberg et al. .............. 424/47 |
| 5,614,173 | A | * | 3/1997 | Ulmer et al. .................. 424/47 |
| 6,017,860 | A | * | 1/2000 | Sajic et al. |

FOREIGN PATENT DOCUMENTS

| EP | 0 201 342 | 12/1986 |
| EP | 0 521 666 | 1/1993 |
| GB | 2 043 077 | 10/1980 |
| JP | 50-160393 | 12/1975 |
| JP | 51-23530 | 2/1976 |
| JP | 53-15436 | 2/1978 |
| JP | 53-121946 | 10/1978 |
| WO | 95/13788 | * 5/1995 |

OTHER PUBLICATIONS

Martino, G.T et al. (1992), Spray Technology & Marketing, Mar. Issue, pp. 34–39.*

Johnsen, M.A. (1992). Spray Technology & Marketing, Jun. Issue, pp. 32–40.*

* cited by examiner

Primary Examiner—Raj Bawa
(74) Attorney, Agent, or Firm—Sughrue Mion, PLLC

(57) ABSTRACT

A hair cosmetic composition having an excellent hair setting property, and which imparts to hair good flexibility and a good finish feeling. The hair cosmetic composition comprises (a) a water-soluble amine-oxide-containing polymer having a weight-average molecular weight of 10,000 to 500,000 and (b) a water-soluble polymer selected from the group consisting of nonionic, cationic, anionic and amphoteric polymers. The weight ratio of component (a) to component (b) falls within a range of from 1:10 to 10:1. Components (a) and (b) are incorporated in a total amount of from 0.1 to 10 wt. % based on the hair cosmetic composition.

18 Claims, No Drawings

HAIR COSMETIC COMPOSITION CONTAINING AMINE-OXIDE POLYMER

FIELD OF THE INVENTION

This invention relates to a hair cosmetic composition comprising (a) an amine-oxide-containing copolymer and (b) a water-soluble polymer selected from nonionic, cationic, anionic and amphoteric polymers. The composition of the present invention has an excellent hair setting property, and imparts good flexibility and a good finish feeling so that it is useful for applications such as a hair spray, hair mousse, hair setting lotion and hair gel.

BACKGROUND OF THE INVENTION

In order to retain hair in a desired shape, it is a common practice to set hair by applying thereto a solution of a film-forming polymer compound in water or a lower alcohol, or a mixed solvent thereof, and then drying.

Nonionic high-molecular compounds such as polyvinyl pyrrolidone and vinyl pyrrolidone/vinyl acetate copolymer are widely used as the film-forming polymer compounds. Such PVP and PVP/VA copolymers are described in the International Cosmetic Ingredient Dictionary published by The Cosmetic, Toiletry, and Fragrance Association, JP-B-46-19637 (the term "JP-B" as used herein means an "examined published Japanese patent publication") and JP-A-51-144480 (the term "JP-A" as used herein means an "unexamined published Japanese patent application). However, the use of these compounds is accompanied by the following drawbacks. In order to bring about high hair setting effects, the film formed therefrom is hard and lacks flexibility. This stiffens the hair, and under highly humid conditions causes hair to stick. Thus, the subject compounds do not have sufficient hair setting effects. Use of the above compounds is also accompanied by flaking. That is, a phenomenon where the film thus formed is divided into small flakes by combing after hair setting. Also, due to static charge, the hair spreads and cannot be easily set. Judging from these points, the above-exemplified compounds are unsatisfactory.

The use of anionic polymer compounds as the film-forming polymer compounds is also known. However, the film formed therefrom is hard as a result of increasing the hair setting effects, it stiffens the hair due to lack of flexibility, and the resulting hair setting effects are not satisfactory. In addition, its use is accompanied by flaking, and due to static charge, the hair spreads and cannot easily be set. From these points, the anionic polymer compounds are therefore unsatisfactory. To overcome such problems, there has been an attempt to add a cosmetic additive such as oils and fats or a surfactant. However, this brings about further deterioration in the hair setting effects. Thus, a hair cosmetic composition having a well-balanced performance has not yet been prepared using an anionic polymer compound.

Cationic polymer compounds have also been widely used as the film-forming polymer compound to retain the desired hair shape and to improve the touch feeling upon application of the resulting composition. These compounds, however, are disadvantageous in that they do not have sufficient hair setting effects to retain the desired hair shape, and due to the flexibility of the film thus formed, hair having a retained shape lacks resilience particularly under high humidity conditions. Moreover, when the hair cosmetic composition containing a cationic polymer compound is used repeatedly, the cationic polymer compound accumulates on the hair. This causes build-up problems such as deterioration in the combing property or appearance of the hair. Thus, the cationic polymer compound is unsatisfactory as the film-forming compound.

Amphoteric polymer compounds have also come to be widely used as the film-forming polymer compound (JP-A-49-14647, JP-A-51-9732, JP-A-55-104209, etc.). These compounds are unsatisfactory because they stiffen the hair due to lack of flexibility, are unable to retain the desired shape of the hair particularly under high-humidity conditions and therefore do not provide sufficient hair setting effects, and cannot be sufficiently removed by washing. Thus, the amphoteric polymer compounds are also unsatisfactory as the film-forming compound.

To overcome the above-described problems, particularly, to improve hair setting effects and resilience, JP-A-55-59107 proposes a hair cosmetic composition comprising a cationic polymer compound and an anionic polymer, while JP-A-58-124712 proposes a hair cosmetic composition comprising a cationic polymer compound and an amphoteric polymer.

Even the above compositions do not provide satisfactory performance as a hair setting composition in terms of hair setting effects or resilience.

SUMMARY OF THE INVENTION

It is therefore an object of the present invention to provide a hair setting cosmetic composition which overcomes the above-described problems of conventional film-forming polymers such as cationic polymers, anionic polymers, nonionic polymers or amphoteric polymers, which has an excellent hair setting property, and which imparts to hair good resilience and a good finish feeling.

The present inventors found that the above objectives can be obtained by using, as film-forming polymer compounds, a conventional water-soluble polymer compound having a weight-average molecular weight of 5,000 to 500,000 in combination with a novel water-soluble amine-oxide-containing polymer compound, to thereby achieve the present invention.

Thus, the present invention provides a hair cosmetic composition comprising (a) a water-soluble amine-oxide-containing polymer having a weight-average molecular weight of 10,000 to 500,000 and (b) a water-soluble polymer selected from the group consisting of nonionic polymers, cationic polymers, anionic polymers and amphoteric polymers, the weight ratio of said component (a) to said component (b) falling within a range of from 1:10 to 10:1 and said components (a) and (b) being incorporated in a total amount of from 0.1 to 10 wt. % based on the hair cosmetic composition.

In the present invention, the term "water solubility" as used herein means as follows: when an aqueous solution obtained by stirring 1 part by weight of an amine-oxide-containing resin and 99 parts by weight of a deionized water under heat at 60° C. for two hours is uniform even after cooling and being allowed to stand for one day at room temperature; and has, in a 1 cm×1 cm cell, a transmittance of 70% or greater at 655 nm, it is regarded to have water solubility.

The amine-oxide-containing polymer for use as component (a) in the present invention has (a1) a polymer structure composed of an amine-oxide-containing unsaturated monomer or has (a2) a polymer structure composed of an amine-oxide-containing unsaturated monomer and a hydrophobic unsaturated monomer. A copolymer structure composed of 15 to 90 wt. % of an amine-oxide-containing monomer and 85 to 10 wt. % of a hydrophobic monomer is preferred.

The term "the component (a1) having a polymer structure composed of an amine-oxide-containing unsaturated monomer" as used herein includes a polymer which is prepared by any one of the processes (1) to (4) described below, to thereby obtain a polymer comprising structural units containing an amine-oxide group.

Among the processes described below, (2) is preferred for preparing the amine-oxide-containing polymer (a1).

(1) A process of polymerizing an amine-oxide-containing monomer (A) obtained by forming an oxide of a nitrogen-containing monomer.

(2) A process of polymerizing a nitrogen-containing monomer, followed by forming an oxide of the nitrogen-containing group.

(3) A process of polymerizing a monomer having a reaction-active functional group, followed by reacting with a substance containing both a group reactive with the functional group and an amine-oxide group.

(4) A process of polymerizing a monomer having a reaction-active functional group, followed by reacting with a substance containing both a group reactive with the functional group and a nitrogen-containing group, and then forming an oxide of the nitrogen-containing group.

The term "the component (a2) having a copolymer structure composed of an amine-oxide-containing unsaturated monomer and a hydrophobic unsaturated monomer" as used herein includes a polymer which is prepared by any one of processes (5) to (8) described below, to thereby obtain a polymer containing structural units derived from a monomer containing an amine-oxide group and a hydrophobic unsaturated monomer.

Among these processes, (6) is preferred for preparing the amine-oxide-containing polymer (a2).

(5) A process of copolymerizing an amine-oxide-containing monomer (A) obtained by forming an oxide of a nitrogen-containing monomer, and a hydrophobic unsaturated monomer (B).

(6) A process of copolymerizing a nitrogen-containing unsaturated monomer and a hydrophobic unsaturated monomer (B), followed by forming an oxide of the nitrogen-containing group.

(7) A process of copolymerizing a monomer having a reaction-active functional group and a hydrophobic unsaturated monomer (B), followed by reacting with a substance having both a group reactive with the functional group and an amine oxide group.

(8) A process of copolymerizing a monomer having a reaction-active functional group and a hydrophobic unsaturated monomer (B), followed by reacting with a substance having both a group reactive with the functional group and a nitrogen-containing group and then forming an oxide of the nitrogen-containing group. Amine-oxide-containing monomer (A):

Examples of the amine-oxide-containing monomer as component (A) include monomers represented by the following formulas (I) to (IV):

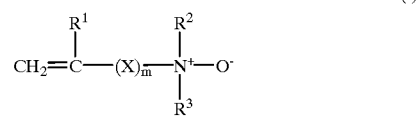

(I)

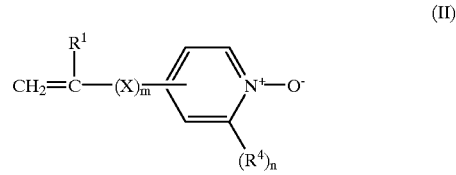

(II)

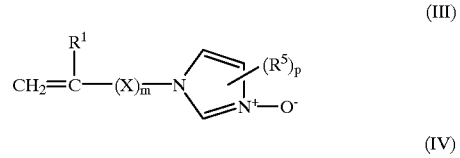

(III)

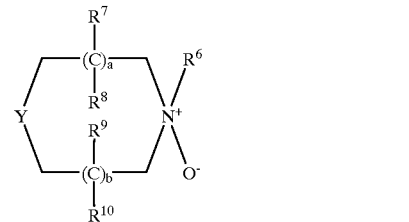

(IV)

wherein $R^1$ represents a hydrogen atom or a methyl group, $R^2$ and $R^3$ are the same or different and each independently represents a $C_{1-24}$ alkyl group $C_{6-24}$ aryl group or $C_{7-24}$ arylalkyl group, $R^4$ and $R^5$ each independently represents a $C_{1-24}$ alkyl group, $C_{6-24}$ aryl group or $C_{7-24}$ arylalkyl group, X represents a divalent linking group, m is 0 or 1, n is an integer of 0 to 4 and p is an integer of 0 to 3, Y represents

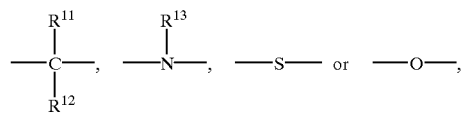

in which at least one of $R^6$ to $R^{13}$ represents

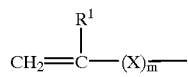

and the other of $R^6$ to $R^{13}$ each represents a hydrogen atom, $C_{1-24}$ alkyl group, $C_{6-24}$ aryl group or $C_{7-24}$ arylalkyl group, and a and b are the same or different and each independently represents an integer of 1 to 10.

Examples of the monomer represented by formula (I) include amine-oxide-introduced products obtained by forming the oxide of the nitrogen atom of N,N-dimethylaminoethyl acrylate, N,N-dimethylaminoethyl methacrylate (which is hereinafter abbreviated as N,N-dimethylaminoethyl (meth)acrylate), N,N-diethylaminoethyl (meth)acrylate, N,N-dimethylaminopropyl (meth)acrylate, N,N-diethylaminopropyl (meth)acrylate, N,N-dimethylaminoethyl (meth)acrylamide, N,N-diethylaminoethyl (meth)acrylamide, N,N-dimethylaminopropyl (meth)acrylamide, N,N-diethylaminopropyl (meth)acrylamide, vinyl N,N-dimethylaminorpropionate, p-dimethylaminomethylstyrene, p-dimethylaminoethylstyrene, p-diethylaminomethylstyrene and p-diethylaminoethylstyrene; amine-oxide introduced products obtained by forming the oxide of the nitrogen atom of the reaction product between an unsaturated-containing acid anhydride such as maleic anhydride, itaconic anhydride or crotonic anhydride and N,N-dimethyl-1,3-propaneamine or N,N-dimethyl-p-phenylenediamine having both a group reactive with the acid anhydride group and a tertiary amino group; and amine-oxide-introduced products obtained by forming the oxide of the nitrogen atom of the reaction product between an epoxy-containing monomer such as glycidyl methacrylate and a compound such as N,N-dimethyl-1,3-propaneamine or N,N-dimethyl-p-phenylenediamine having both a group reactive with the epoxy group and a tertiary amino group. Examples also include products obtained by reacting an epoxy-containing monomer such as glycidyl methacrylate and an amine-oxide containing compound, such as hydroxyethyl-N,N-dimethylamineoxide, containing a group reactive with the epoxy group; and products obtained by reacting an isocyanate-containing monomer such as 2-isocyanate ethyl (meth)acrylate and an amine-oxide-containing compound, such as hydroxyethyl-N,N-dimethylaminoxide, containing a group reactive with the isocyanate group.

Examples of the monomer represented by formula (II) include amine-oxide-introduced products obtained by forming the oxide of the nitrogen atom of alkyl-, aryl- or alkylaryl-added compounds such as 2-vinylpyridine, 3-vinylpyridine, 4-vinylpyridine, 2-methyl-5-vinylpyridine, 3-methyl-5-vinylpyridine, 4-methyl-5-vinylpyridine, 6-methyl-5-vinylpyridine, 2-methyl-4-vinylpyridine, 3-methyl-4-vinylpyridine, 2-lauryl-5-vinylpyridine, 2-lauryl-4-vinylpyridine, 2-(t-butyl)-5-vinylpyridine or 2-(t-butyl)-4-vinylpyridine.

Examples of the monomer represented by formula (III) include amine-oxide-introduced products obtained by forming oxide of the nitrogen atom of 1-vinylimidazole, 2-methyl-1-vinylimidazole, 4-methyl-1-vinylimidazole, 5-methyl-1-vinylimidazole, 2-lauryl-1-vinylimidazole and 4-(t-butyl)-1-vinylimidazole.

Examples of the monomer represented by formula (IV) include amine-oxide-introduced products such as 4-vinylmorpholine, 2-methyl-4-vinylmorpholine, 4-arylmorpholine, 1-vinylpiperidine, 4-methyl-4-vinylpiperidine, 2-lauryl-1-vinylpiperazine and 4-methylpiperazinoethyl methacrylate.

Among them, monomers represented by formula (I) are most preferred, and a (meth)acryloyloxyalkylene compound in which $R^2$ and $R^3$ each independently represents a $C_{1-4}$ alkyl group in formula (I) is particularly preferred.

Nitrogen-containing Monomer

Examples of the nitrogen-containing monomer before oxide formation include monomers represented by the following formulae (VI) to (IX):

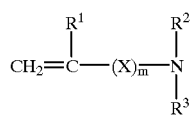

(VI)

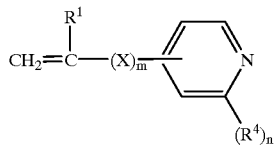

(VII)

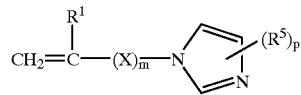

(VIII)

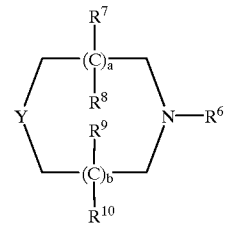

(IX)

wherein $R^1$–$R^{10}$, a, b, m, n, p, X and Y have the same meanings as defined in the above formulae (I) to (IV).

The amine-oxide-containing monomer may be replaced with a hydrophilic monomer other than the component (A) (component (C)) in an amount of 30 wt. % or less.

Hydrophilic Monomer (C)

Examples of the hydrophilic monomer include nonionic, anionic and cationic monomers and amphoteric monomers having both anionic and cationic properties in a single molecule.

Among them, specific examples of the nonionic monomer include (meth)acrylonitrile, N-cyclohexylmaleimide, N-phenylmaleimide, N-vinylpyrrolidone, N-vinylformamide, N-vinylacetamide, N-(meth)acryloyl morpholine; monomers derived from a (meth)acrylic acid or (meth)acrylamide and a $C_{2-4}$ alkylene oxide, such as hydroxyethyl (meth)acrylate, polyethylene glycol (meth) acrylate, methoxypoly(ethylene glycol/propylene glycol) mono(meth)acrylate, polyethylene glycol di(meth)acrylate or N-polyoxyalkylene (meth)acrylamide; and hydrophilic monomers such as (meth)acrylamide.

Specific examples of the anionic monomer include unsaturated carboxylic acid monomers such as (meth)acrylic acid, maleic acid, maleic anhydride, itaconic acid, fumaric acid and crotonic acid; half esters of an unsaturated polybasic anhydride (e.g., succinic anhydride, phthalic anhydride) and a hydroxyl-containing (meth)acrylate such as hydroxyethyl (meth)acrylate; monomers containing a sulfonic acid group such as sulfoethyl (meth)acrylate and monomers containing a phosphoric acid group such as acid phosphoxyethyl (meth) acrylate.

The above-exemplified anionic unsaturated monomer can be used as an acid or after being partially or completely neutralized with a basic compound. It is also possible to provide the monomer for copolymerization as an acid, followed by partially or completely neutralizating with a basic compound. Examples of the basic compound for the neutralization include hydroxides of an alkali metal such as sodium hydroxide or potassium hydroxide; inorganic basic compounds such as aqueous ammonia; alkanolamines such as ethanolamine, diethanolamine, triethanolamine, triisopropanolamine, 2-amino-2-methyl-1-propanol, 2-amino-2-methyl-1,3-propanediol and aminomercaptopropane diol; and basic amino acid compounds such as lysine, arginine and histidine.

Examples of the cationic monomer include those obtained by cationizing a tertiary-amino-containing monomer such as N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminoethyl (meth)acrylamide, N,N-diethylaminoethyl (meth)acrylamide, N,N-dimethylaminopropyl (meth)acrylamide, N,N-diethylaminopropyl (meth)acrylamide, p-dimethylaminomethylstyrene, p-dimethylaminoethylstyrene, p-diethylaminomethylstyrene or p-diethylaminoethylstyrene with a cationizing agent, for example, a halogenated alkyl such as methyl chloride, methyl bromide or methyl iodide, a dialkylsulfuric acid such as dimethylsulfuric acid, an epichlorohydrin-added tertiary amine mineral acid salt such as N-(3-chloro-2-hydroxypropyl)-N,N,N-trimethylammonium chloride, an inorganic salt such as hydrochloric acid, hydrobromic acid, sulfuric acid or phosphoric acid, or a carboxylic acid such as formic acid, acetic acid or propionic acid.

Examples of the amphoteric unsaturated monomer include amphoteric ion monomers obtained by making amphoteric a tertiary-amino-containing monomer, which is a precursor of the above-described cationic monomer, using a denaturant such as a monohalofatty acid salt, for example, potassium monochloroacetate, sodium monochloroacetate or potassium monobromopropionate, propiolactone, butyrolactone or propansultone.

The amine-oxide-containing polymer for use as component (a) in the present invention preferably is a copolymer having a weight-average molecular weight of 10,000 to 500,000, and is composed of 15 to 90 wt. % of an amine-oxide-containing unsaturated monomer (A) and 85 to 10 wt. % of a hydrophobic unsaturated monomer (B).

When the amount of the component (A) is smaller than 15 wt. %, the water solubility of the resulting copolymer is reduced, resulting in the problem that the copolymer is not easily washed away at the time of hair washing. Amounts greater than 90 wt. %, on the other hand, make the hair sticky. Amounts outside the above range are therefore not preferred.

Hydrophobic Monomer (B)

Examples of the hydrophobic monomer (B) include hydrophobic vinyl monomers such as $C_{1-24}$ alkyl (meth) acrylates, styrene, p-methylstyrene, p-chlorostyrene, vinyl methyl ether, vinyl cyclohexyl ether, vinyl acetate, diethyl maleate and dibutyl maleate, glycidyl (meth)acrylate and fluoroalkyl esters of (meth)acrylic acid. Examples also include macromonomers such as radical- polymerizable unsaturated-group-containing silicone macromonomers.

Specific examples of the above-described $C_{1-24}$ alkyl (meth)acrylate include methyl (meth)acrylate, ethyl (meth) acrylate, propyl (meth)acrylate, isopropyl (meth)acrylate, butyl (meth)acrylate, isobutyl (meth)acrylate, secondary-butyl (meth)acrylate, tertiary-butyl (meth)acrylate, pentyl (meth)acrylate, secondary-pentyl (meth)acrylate, 1-ethylpropyl (meth)acrylate, 2-methylbutyl (meth)acrylate, isopentyl (meth)acrylate, tertiary-pentyl (meth)acrylate, 3-methylbutyl (meth)acrylate, neopentyl (meth)acrylate, hexyl (meth)acrylate, 2-methylpentyl (meth)acrylate, 4-methylpentyl (meth)acrylate, 2-ethylbutyl (meth)acrylate, cyclopentyl (meth)acrylate, cyclohexyl (meth)acrylate, heptyl (meth)acrylate, 2-heptyl (meth)acrylate, 3-heptyl (meth) acrylate, octyl (meth)acrylate, 2-octyl (meth)acrylate, 2-ethylhexyl (meth)acrylate, isooctyl (meth)acrylate, nonyl (meth)acrylate, 3,3,5-trimethylhexyl (meth)acrylate, decyl (meth)acrylate, undecyl (meth)acrylate, lauryl (meth) acrylate, cetyl (meth)acrylate, stearyl (meth)acrylate, eicosyl (meth)acrylate, docosyl (meth)acrylate, tetracosyl (meth) acrylate, methylcyclohexyl (meth)acrylate, isobornyl (meth) acrylate, norbornyl (meth)acrylate, benzyl (meth)acrylate and phenetyl (meth)acrylate.

Among them, $C_{1-24}$ alkyl (meth)acrylates represented by the following formula (V) are preferred.

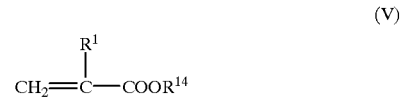

(V)

wherein $R^1$ represents a hydrogen atom or a methyl group and $R^{14}$ represents a $C_{1-24}$ alkyl group.

The component (B) is preferably added in an amount of 10 to 85 wt. %. When the amount exceeds 85 wt. %, the copolymer film has deteriorated smoothness and transparency and moreover, becomes sparingly soluble in water so that it is not easily washed away at the time of hair washing. Amounts smaller than 10 wt. %, on the other hand, make the hair sticky. Amounts outside the above range are therefore not preferred.

Polymerization Process

An amine-oxide-containing resin can be obtained by polymerizing the above-described monomer components by known methods such as solution polymerization, bulk polymerization or suspension polymerization generally in the presence of a radical polymerization initiator. The solution polymerization method is particularly suitable. Examples of the solvent that can be used for polymerization include organic solvents such as acetone, methyl ethyl ketone, methyl isobutyl ketone, methanol, ethanol, propanol, isopropanol, butanol, isobutanol, secondary butanol, ethyl acetate, propyl acetate or butyl acetate. These solvents may be used either singly or in combination. The solvent is preferably used in an amount needed to provide a polymer concentration of 10 to 65 wt. % in the resulting copolymer solution.

Examples of the radical polymerization initiator include azo compounds such as 2,2'-azobisisobutyronitrile (AIBN), 2,2'-azobis(2,4-dimethylvaleronitrile), 2,2'-azobis(4-methoxy-2,4-dimethylvaleronitrile), dimethyl-2,2'-azobisisobutyrate, 2,2'-azobis(2-methylbutyronitrile) or 1,1'-azobis(1-cyclohexanecarbonitrile) and peroxides such as benzoyl peroxide, dicumyl peroxide, di-t-butyl peroxide and lauroyl peroxide. The polymerization initiator may generally be added in an amount of 0.01 to 5 wt. % based on the total amount of components (A) to (C).

The polymerization is generally carried out at 30 to 120° C., preferably 40 to 100° C. for 1 to 20 hours in an inert gas atmosphere such as nitrogen or argon. It is a common practice to charge the entire amount of all the monomers at the beginning of the polymerization, but it is also possible to add these monomers in portions by kind and/or weight.

Oxide Formation

An amine-oxide-containing resin is obtained by adding an oxide forming agent to a resin solution obtained by the polymerization of monomer components at 20 to 100° C. for 0.1 to 100 hours, preferably 1 to 50 hours.

An oxidizing agent such as peroxide or ozone is used as the oxide forming agent for the resulting precursor. Specific examples of the peroxide include hydrogen peroxide, ammonium persulfate, sodium persulfate, peracetic acid, metachloroperbenzoic acid, benzoyl peroxide and t-butyl hydroperoxide, however, hydrogen peroxide is ordinarily used. The oxide forming agent is used in a molar equivalent amount of from 0.2 to 3 times relative to the functional group which is able to form an oxide in the precursor polymer, with a molar equivalent amount of 0.5 to 2 times being more preferred. The remaining portion of peroxide can be used without treatment or after treating with a known method. Specific examples of such treatment include the addition of a reducing agent or a metal catalyst, ion exchange treatment and treatment with activated charcoal.

The resin solution thus obtained can be used as is. It can also be used after isolating an amine-oxide-containing resin in a known manner such as by precipitation or removal of solvent by distillation. The isolated amine-oxide-containing resin can be further purified as needed by reprecipitation, solvent washing, membrane separation or adsorption treatment.

The resin thus obtained generally has a weight-average molecular weight of 10,000 to 500,000. Weight-average molecular weights of less than 10,000 reduce the hair setting property. Those greater than 500,000, on the other hand, deteriorate compatibility with water or the like and increase the viscosity of the solution. This results in problems of working efficiency or coating properties. (b) Water-soluble high-molecular polymers The water-soluble polymer of component (b) is selected from nonionic polymers (b1), cationic polymers (b2), anionic polymers (b3) and amphoteric polymers (b4), and has a weight average molecular weight of 5,000 to 500,000, preferably 10,000 to 100,000.

In the present invention, the term "water solubility" as used herein means as follows: when an aqueous solution obtained by stirring 1 part by weight of polymer selected from (b1) to (b4) and 99 parts by weight of a deionized water under heat at 60° C. for two hours is uniform even after cooling and being allowed to stand for one day at room temperature; and has, in a 1 cm×1 cm cell, a transmittance of 70% or greater at 655 nm, it is regarded to have water solubility.

(b1) Nonionic Polymers

The nonionic polymer is a polymer having as an essential component a repeating unit derived from an unsaturated monomer containing a pyrrolidone ring, caprolactam ring, amide group, N-alkyl-substituted amide group, polyether group, acetamide group or formamide group. Specific examples of the polymer containing a pyrrolidone ring include polyvinyl pyrrolidone such as "Luviskol K-12, K-17, K-30, K-60, K-80 and K-90"(each, trade name; product of BASF AG) and "PVP K-15, K-30, K-60, K-90 and K-120" (each, trade name; product of ISP, Inc.); vinyl pyrrolidone/vinyl acetate copolymers such as "Luviskol VA28, VA37, VA55, VA64 and VA73" (each, trade name; product of BASF AG), "PVP/VA-735, PVP/VA-635, PVP/VA-535, PVP/VA-335, PVP/VA-235, S-630" (each trade name, product of ISP, Inc.); and vinyl pyrrolidone/vinyl acetate/vinyl propionate copolymers such as "Ruviskol VAP343" (trade name; product of BASF AG).

Specific examples of the polymer containing as an essential component a repeating unit derived from an amide-, N-alkyl-substituted-amide- or polyether-containing unsaturated monomer include radical homopolymers of an unsaturated monomer such as (meth)acrylamide, N-octyl (meth)acrylamide, hydroxyethyl (meth)acrylate, (meth)acrylic acid methoxypolyethylene glycol, (meth)acrylic acid methoxypolyethylene glycol.polypropylene glycol; and radical copolymers with a $C_{1-24}$ alkyl (meth)acrylate, vinyl acetate or the like.

(b2) Cationic Polymers

Specific examples of the synthetic cationic polymer include N-vinyl pyrrolidone/quaternized dimethylaminoethyl methacrylate copolymers such as "Gafquat 755N, 755 and 734" (each, trade name; product of ISP, Inc.) and "Ruviquat PQ11" (trade name; product of BASF AG); N-vinyl pyrrolidone/dimethylaminoethyl methacrylate copolymers such as "Copolymer 845, 937 and 958" (each, trade name; product of ISP, Inc.); N-vinyl pyrrolidone/N-vinyl caprolactam/dimethylaminoethyl methacrylate copolymers such as "Gafix VC-713" (trade name; product of ISP, Inc.); N-vinyl pyrrolidone/methacrylamidopropyl trimethylammonium chloride copolymer such as "Gafquat HS-100" (trade name; product of ISP, Inc.); N-vinyl pyrrolidone/quaternized methylvinyl imidazolium copolymer such as "Luviquat FC370, FC550, FC905 and HM-552" (each, trade name; product of BASF AG.); dimethyldiallylammonium chloride polymers and dimethyldiallylammonium chloride/acrylamide copolymers such as "Merquat 100 and 550" (trade name; Calgon); and quaternized dialkylaminoalkylene methacrylate/alkyl (meth)acrylate copolymers as disclosed in JP-A-4-21623 or JP-A-5-310538.

Examples of the cationic polymer obtained by modifying a natural product include hydroxyethyl cellulose/dimethyldiallyl ammonium chloride copolymers such as "Cellquat H-100 and L200" (each, trade name; product of National Starch Inc.); reaction products of hydroxyethyl cellulose with an epoxylated trimethyl ammonium compound such as "Cellquat SC-240, SC-240C and SC-230M" (each, trade name; product of National Starch Inc.), "Ucare Polymer JR-125, JR-400 and JR-30M" (each, trade name; product of Amerchol); Reoguard G (trade name; product of Lion Corp.) and "Catinal HC and LC" (trade name; product of Toho Chemical Industry Co.); and quaternized chitosan such as "Kytamer PC" (trade name; product of Amerchol).

(b3) Anionic polymers

Anionic polymers are polymers having an acid group such as a carboxyl or sulfonic acid group. Specific examples include methyl vinyl ether/maleic anhydride alkyl half ester copolymers such as "Gantrez ES-225, ES-425, A-425, V-225 and V-425" (each, trade name; product of ISP, Inc.); vinyl acetate/crotonic acid/vinyl neodecanoate copolymers such as "Resin 28-131" (trade name; National Starch Inc.) and "Luviset CA" (trade name; product of BASF AG); vinyl acetate/crotonic acid/vinyl neodecanoate copolymers such as "Resin 28-2930" (trade name; product of National Starch Inc.); vinyl acetate/monobutyl maleate/isobornyl acrylate copolymers such as "ADVANTAGE CP" (trade name; product of ISP, Inc.); (meth)acrylic acid/(meth)acrylic ester copolymers such as "Ruvimer 100P" (trade name; product of BASF AG) and "Diahold" (trade name; Mitsubishi Chemical); acrylic acid/acrylamide derivative copolymers such as "Ultrahold Strong and Ultrahold 8" (each, trade name; product of BASF AG), "Versatile 42" (trade name; product of National Starch Inc.) and "Plus Size L53P" (trade name; product of GOO Chemical); polyvinyl pyrrolidone/(meth)acrylic acid/(meth)acrylic ester copolymers such as "Luviflex VBM35" (trade name; product of BASF AG); and diethylene glycol/cyclohexane dimethanol/dimethyl isophthalate/sulfonated dimethyl isophthlate condensates such as "Eastman AQ Polymer" (Eastman Chemical).

From the viewpoint of water solubility, the anionic copolymer is preferably used after its acid group is partially or wholly neutralized with a basic compound. Examples of such a basic compound include hydroxide of an alkali metal such as sodium hydroxide and potassium hydroxide, inorganic basic compounds such as aqueous ammonia, alkanolamines such as ethanolamine, diethanolamine, triethanolamine, triisopropanolamine, 2-amino-2-methyl-1-propanol, 2-amino-2-methyl-1,3-propanediol and aminomercaptopropanediol; and basic amino acid compounds such as lysine, arginine and histidine. Among them, 2-amino-2-methyl-1-propanol and potassium hydroxide are preferred from the viewpoint of water solubility.

(b4) Amphoteric Polymers

Amphoteric polymers are polymers each containing as an essential component a repeating unit derived from an unsaturated monomer which contains a betaine structural group such as a carboxybetaine group, sulfobetaine group or phosphobetaine group; or polymers each containing as essential components both a repeating unit derived from an unsaturated monomer which contains an anionic group such as a carboxyl group, sulfonic acid group or phosphoric acid group and a repeating unit derived from an unsaturated monomer which contains a quaternary ammonium salt or a tertiary amino group. Specific examples of the polymer containing as an essential component a repeating unit derived from a betaine-structural-group-containing unsaturated monomer include methacrylic carboxybetaine polymers, which are dimethylaminoethyl methacrylate/alkyl methacrylate copolymers modified with a monohaloacetate, for example, "Yukaformer 205A, SM, AMPHOSET, 201, R102, R402, 510, 201, W (each, trade name; product of Mitsubishi Chemical). This technology is disclosed in JP-A-51-9732, JP-A-55-104209, JP-A-61-258804 and JP-7-285832.

Examples of the polymer which comprises as essential components both a repeating unit derived from an unsaturated monomer containing an anionic group such as a carboxyl, sulfonic acid or phosphoric acid group and a repeating unit derived from an unsaturated monomer containing a quaternary ammonium salt or a tertiary amino group include hydroxypropyl acrylate/butylaminoethyl methacrylate/octylamide acrylate copolymers such as "Amformer 28-4910, LV-71 and LV-47" (each, trade name; product of National Starch Inc.), which are polymers each comprising as essential components both a repeating unit derived from a carboxyl-containing unsaturated monomer and a repeating unit derived from a tertiary-amino-containing unsaturated monomer; and diallyldimethylammonium chloride/acrylic acid copolymers such as "Merquat 295" (trade name; product of Calgon), and diallyldimethylammonium chloride/acrylic acid/acrylamide copolymers such as "Merquat Plus 3330" (trade name; product of Calgon), which are polymers comprising as essential components both a repeating unit derived from a carboxyl-containing unsaturated monomer and a repeating unit derived from a quaternary-ammonium-salt-containing unsaturated monomer.

Composition Ratio

In the hair cosmetic composition of the present invention, the weight ratio of the amine-oxide-containing copolymer of component (a) to the nonionic polymer of component (b1) falls within a range of from 1:10 to 10:1, preferably from 1:5 to 10:1. When the weight ratio is less than 1:10, the resulting composition has insufficient flexibility, makes the hair sticky, has insufficient hair setting effects and causes problems such as flaking when combed or difficulty in setting the hair into a desired shape due to static electricity. When the above ratio exceeds 10:1, the resulting composition cannot impart sufficient hardness so that the hair thus set lacks tautness and has a heavy finish feeling, resulting in deterioration of the touch feeling thus obtained. The total amount of components (a) and (b) in the hair cosmetic composition is 0.1 to 10 wt. %, preferably 0.5 to 8%, based on the total weight of the hair cosmetic composition. Amounts of less than 0.1 wt. % provide an insufficient hair setting property, while those exceeding 10 wt. % increase stiffness and deteriorate the touch feeling.

The weight ratio of the amine-oxide-containing copolymer of component (a) to the cationic polymer of component (b2) is within a range of from 1:10 to 10:1, with 1:5 to 10:1 being preferred. When the ratio of (a) to (b2) is less than 1:10, the hair setting effects are insufficient. This prevents the retention of a desired hair shape, and hair that is set with such a composition does not have sufficient resilience under high humidity conditions and becomes sticky. Moreover, repeated use of the composition over a long time period causes problems such as build-up. When the ratio exceeds 10:1, on the other hand, hair that is set with the resulting cosmetic composition cannot be easily combed due to lack of a sliding feeling, and moreover, the smoothness after drying is insufficient. The total amount of components (a) and (b2) is 0.1 to 10 wt. %, preferably 0.5 to 8 wt. %, based on the total amount of the hair cosmetic composition. Amounts of less than 0.1 wt. % lead to insufficient hair setting power, while those exceeding 10 wt. % increase stiffness and deteriorate the touch feeling.

The weight ratio of the amine-oxide-containing polymer of component (a) to the anionic polymer (b3) is 1:10 to 10:1, preferably 1:5 to 10:1. When the ratio is less than 1:10, the resulting cosmetic composition has insufficient flexibility, makes the hair stiff and provides insufficient hair setting effects. This leads to flaking upon combing, and difficulty in setting the hair to a desired shape due to static electricity. When the ratio exceeds 10:1, on the other hand, the resulting composition does not impart sufficient hardness so that the hair thus set lacks tautness and has a heavy (deteriorated) finish feeling. The total amount of components (a) and (b3) is 0.1 to 10 wt. %, preferably 0.5 to 8%, based on the total weight of the hair cosmetic composition. Amounts of less than 0.1 wt. % result in an insufficient hair setting property, while those exceeding 10 wt. % increase stiffness, to thereby deteriorate the feeling touch.

The weight ratio of the amine-oxide-containing polymer of component (a) to the amphoteric polymer (b4) is 1:10 to 10:1, preferably 1:5 to 10:1. When the ratio is less than 1:10, the resulting cosmetic composition has insufficient flexibility, makes the hair stiff, has insufficient hair setting effects to retain a desired shape under high humidity conditions, and is not adequately removed by hair washing. When the ratio exceeds 10:1, on the other hand, the resulting composition does not impart sufficient hardness so that the hair thus set lacks tautness and has a heavy finish feeling, resulting in deterioration of the touch feeling thus obtained. In addition, upon combing after setting the hair with the composition, flaking occurs in which the film thus formed is divided into small flakes. The total amount of components (a) and (b4) is 0.1 to 10 wt. %, preferably 0.5 to 8%, based on the total weight of the cosmetic composition. Amounts of less than 0.1 wt. % result in insufficient hair setting effects, while those exceeding 10 wt. % increase stiffness, to thereby deteriorate the touch feeling.

In the hair cosmetic composition, the amine-oxide-containing polymer (a) having a weight-average molecular weight of 10,000 to 500,000 is preferably used in an amount of 0.1 to 9 wt. %, with 0.1 to 5 wt. % being more preferred; and the water-soluble polymer (b) is preferably used in an amount of 0.1 to 9 wt. %, with 0.1 to 5 wt. % being more preferred.

The water-soluble polymers (b1), (b2), (b3) and (b4) of the component (b) can be used in combination insofar as the combination does not cause gelation. Examples of such combinations include (b1) and (b2); (b1), (b2) and (b4); (b1) and (b3); (b1) and (b4); (b2) and (b4); (b3) and (b4).

In addition to the above-described essential components (a) and (b), it is possible to incorporate into the cosmetic composition of the present invention the following components which are ordinarily used in cosmetic compositions to the extent of not impairing the advantages of the present invention. Examples thereof include glycerides such as castor oil, cacao oil, mink oil, avocado oil, jojoba oil, macadamia nut oil and olive oil; waxes such as beeswax and lanolin, hydrocarbons such as fluid paraffin, solid paraffin isoparaffin and squalane; linear or branched higher alcohols such as cetyl alcohol, oleyl alcohol, stearyl alcohol, isostearyl alcohol, lauryl alcohol and 2-octyl dodecanol; polyvalent alcohols such as ethylene glycol, polyethylene glycol, propylene glycol, polypropylene glycol, glycerin and sorbitol; ethylene oxide and/or propylene oxide adducts of a higher alcohol such as polyoxyethylene lauryl ether, polyoxypropylene cetyl ether and polyoxyethylene polyoxypropylene stearyl ether; esters such as isopropyl myristate, octyldodecyl myristate, hexyl laurate and cetyl lactate; amides such as oleic diethanolamide and lauric diethanolamide; silicone derivatives such as dimethyl polysiloxane, methylphenyl polysiloxane, polyether-modified silicone and amino-modified silicone; cationic surfactants such as stearyl trimethylammonium chloride, distearyl dimethylammonium chloride and lauryl trimethylammonium chloride; anionic surfactants such as polyoxyethylene laurylether sulfate and polyoxyethylene lauryl sulfosuccinate salt; amphoteric surfactants such as lauryl hydroxysulfobetaine and lauryl dimethylcarboxybetaine; protein derivatives and amino acid derivatives such as collagen hydrolyzates, keratin hydrolyzates and polyamino acid; vegetable extracts, crude drugs, vitamins and ultraviolet absorbers such as oxybenzene, chelating agents such as EDTA-Na, antiseptics such as paraben, antioxidants, colorants, pigments and perfumes.

No particular limitation is imposed on the application or form of the hair cosmetic composition of the present invention. It can be used in the form of an aerosol hair spray, hair spray pump, hair spray foam, hair mist, setting lotion, hair gel, hair cream or hair oil.

The hair cosmetic composition of the present invention can be prepared by dissolving or dispersing its constituent components including the above-described components (a) and (b) in a solvent such as water and/or an alcohol such as ethanol or isopropanol in a manner well known to those of ordinary skill in the art. The hair cosmetic composition in each form can be prepared according to the following formulation.

| (i) Hair mousse which can be injected as a foam | |
|---|---|
| (a) water-soluble amine-oxide-containing polymer having a weight average molecular weight of 10,000 to 500,000 | 0.1 to 9 wt. % |
| (b) water-soluble polymer selected from non-ionic, cationic, anionic and amphoteric polymers | 0.1 to 9 wt. % |
| (c) nonionic surfactant | 0.1 to 5 wt. % |
| (d) liquefied gas | 3 to 25 wt. % |
| (e) water-soluble solvent | at least 60 wt. % (balance) |
| (ii) Hair spray | |
| (a) water-soluble amine-oxide-containing polymer having a weight average molecular weight of 10,000 to 500,000 | 0.1 to 9 wt. % |
| (b) water-soluble polymer selected from non-ionic, cationic, anionic and amphoteric polymers | 0.1 to 9 wt. % |
| (f) organic solvent having a boiling point of 50 to 300° C. | 30 to 80 wt. % |
| (g) propellant | 10 to 60 wt. % |
| (iii) Hair gel | |
| (a) water-soluble amine-oxide-containing polymer having a weight average molecular weight of 10,000 to 500,000 | 0.1 to 9 wt. % |
| (b) water-soluble polymer selected from non-ionic, cationic, anionic and amphoteric polymers | 0.1 to 9 wt. % |
| (h) gel base | 0.1 to 3 wt. % |
| (i) water | at least 72 wt. % (balance) |
| (iv) Hair setting lotion | |
| (a) water-soluble amine-oxide-containing polymer having a weight average molecular weight of 10,000 to 500,000 | 0.1 to 9 wt. % |
| (b) water-soluble polymer selected from non-ionic, cationic, anionic and amphoteric polymers | 0.1 to 9 wt. % |
| (j) water-soluble solvent | the remaining portion (at least 50 wt. and not more than 90 wt. %) |
| (v) Hair shampoo | |
| (a) water-soluble amine-oxide-containing polymer having a weight average molecular weight of 10,000 to 500,000 | 0.01 to 3 wt. % |
| (b) water-soluble polymer selected from non-ionic, cationic, anionic and amphoteric polymers | 0.01 to 3 wt. % |
| (c) surfactant selected from anionic, nonionic and amphoteric surfactants | 0.01 to 1 wt. % |
| (e) water | at least 95 wt. % (balance) |
| (vi) Hair rinse | |
| (a) water-soluble amine-oxide-containing polymer having a weight average molecular weight of 10,000 to 500,000 | 0.05 to 3 wt. % |
| (b) water-soluble polymer selected from cationic, anionic and amphoteric polymers | 0.01 to 3 wt. % |
| (c) nonionic surfactant | 0.01 to 1 wt. % |
| (e) water-soluble solvent | at least 95 wt. % (balance) |

Examples of the surfactant (c) for use in the shampoo or rinse include anionic surfactants such as N-(fatty acid acyl)-N-methyl-β-alanine salts, e.g., N-cocoyl-N-methyl-βalanine sodium and N-myristoyl-N-methyl-β-alanine sodium; amphoteric surfactants such as cocoacidpropylbetaine, dimethyllaurylbetaine, bis(2-hydroxyethyl)laurylbetaine, cyclic laurylamine oxide, dimethyllaurylamine oxide and bis(2-hydroxyoxyl)laurylamine oxide; nonionic surfactants such as stearic diethanol amide, coconut oil fatty acid diethanol amide, sorbitan sesquioleate and polyoxyethylene stearyl ether; and cationic surfactants such as stearyltrimethylammonium chloride, distearyldimethylammonium chloride and stearyldimethylbenzylammonium chloride.

Examples of the nonionic surfactant (c) for use in the hair mousse include sorbitan fatty acid ester, glycerin fatty acid ester, polyoxyethylene sorbitan fatty acid ester, polyethylene glycol fatty acid ester, polyoxyethylene alkyl ether, polyoxyethylene alkyl phenyl ether, polyoxyethylene castor oil, polyoxyethylene hydrogenated castor oil and fatty acid alkanol amide.

Examples of the liquefied gas (d) for use in the hair mousse include liquefied petroleum gas, dimethyl ether, trichloromonofluoromethane and dichlorodifluoromethane. Examples of the propellant (g) for use in the hair spray include liquefied gases such as liquefied petroleum gas, dimethyl ether and halogenated hydrocarbon and compressed gases such as air, carbon dioxide gas and nitrogen gas.

As the water-soluble solvent (e), water, ethanol or isopropanol can be used, with water being mainly used.

Examples of the organic solvent having a boiling point of 50 to 300° C. include hydrocarbon alcohols such as ethanol, isopropyl alcohol and ethylene glycol.

The present invention is hereinafter described in greater detail by reference to the following Examples. However, the present invention should not be construed as being limited thereto. All parts and percentages are given by weight unless otherwise indicated.

EXAMPLES

Preparation Example 1

In a reactor equipped with a reflux condenser, dropping funnel, thermometer, nitrogen gas inlet tube and agitator, 50 parts of N,N-dimethylaminoethyl methacrylate, 30 parts of methyl methacrylate, 20 parts of isobutyl methacrylate and 150 parts of absolute ethanol were charged, followed by the addition of 0.6 part of 2,2'-azobisisobutyronitrile. The resulting mixture was reacted at 80° C. for 8 hours under a nitrogen gas atmosphere and was then cooled to 60° C.

To the polymer solution thus obtained, a 31% aqueous solution of hydrogen peroxide was added dropwise through the dropping funnel in an equimolar amount to the N,N-dimethylaminoethyl methacrylate, followed by stirring for 20 hours to form the oxide of the dimethylamino group. Absolute ethanol was added to adjust the polymer concentration to 30%. The completion of oxide formation was confirmed by measuring the amine value of the reaction mixture. The polymer thus obtained was designated as "P-1".

The polymer thus obtained had a weight-average molecular weight of 110,000. In an infrared absorption spectrum of the polymer, the absorption of N-O was observed, to thereby confirm the formation of an amine oxide group.

Preparation Example 2

In a reactor similar to that of Example 1, 70 parts of N,N-dimethylaminoethyl methacrylate, 10 parts of methyl methacrylate, 20 parts of stearyl methacrylate and 100 parts of absolute ethanol were charged, followed by the addition of 0.2 part of 2,2'-azobisisobutyronitrile. After reacting at 80° C. for 8 hours under a nitrogen atmosphere, the reaction mixture was cooled to 60° C.

To the reaction mixture, a 31% aqueous solution of hydrogen peroxide was added dropwise in a molar ratio of 1.2 to the N,N-dimethylaminoethyl methacrylate over a period of one hour, followed by stirring for 15 hours to form an oxide of the dimethylamino group. Absolute ethanol was added to adjust the polymer concentration to 35%. The completion of oxide formation was confirmed by measuring the amine value in the reaction mixture.

Then, 100 parts of the resulting reaction mixture were passed through a column having 50 parts of a regenerated anion exchange resin ("Diaion PA416", trade name) filled therein to treat the remaining portion of hydrogen peroxide.

Preparation Example 3

In a reactor equipped with a reflux condenser, dropping funnel, thermometer, nitrogen gas inlet tube and agitator, 200 parts of N-vinylformamide, 800 parts of pure water and 0.6 part of 2,2'-azobis(2-amidinopropane) dihydrochloride were charged and polymerized at 60° C. for 6 hours under a nitrogen gas atmosphere.

The resulting polymer had a weight-average molecular weight of 150,000. The nonionic polymer thus obtained was designated as "P-3".

Preparation Example 4

In a reactor equipped with a reflux condenser, dropping funnel, thermometer, nitrogen gas inlet tube and agitator, 60 parts of N,N-dimethylaminoethyl methacrylate, 10 parts of methyl methacrylate, 15 parts of butyl methacrylate, 15 parts of stearyl methacrylate and 100 parts of absolute ethanol were charged, followed by the addition of 0.2 part of 2,2'-azobisisobutyronitrile. After reacting the resulting mixture at 80° C. for 8 hours under a nitrogen gas atmosphere, the reaction product was cooled to 45° C.

To the reaction mixture thus obtained, diethylsulfuric acid was added dropwise in an equimolar amount to the N,N-dimethylaminoethyl methacrylate, followed by stirring at 60° C. for an additional 3 hours to cationize the dimethylamino group. Absolute ethanol was added to adjust the polymer concentration to 40%.

The polymer thus obtained had a weight-average molecular weight of 180,000. The cationic polymer thus obtained was designated as "P-4".

Examples 1–6, Comparative Examples 1–4

In each of Examples 1–6 and Comparative Examples 1–4, a hair cosmetic composition (pump spray) having the composition shown in Table 1 was prepared in a manner well known to those of ordinary skill in the art. The hair setting power, hair tautness and flaking at the time of applying the resulting cosmetic composition to the hair, and the antistatic properties (surface resistance) thereof when applied to a polypropylene film were tested and evaluated by the methods described below.

As seen from Table 1, the hair cosmetic compositions of Examples 1 to 6 exhibited excellent hair setting power, and retained a curled hair shape even under high-temperature and humidity conditions. Also, these compositions did not make the hair sticky under such conditions. Furthermore, these compositions imparted to the hair tautness and resilience, and were free from flaking. Moreover, these compositions had excellent antistatic properties.

On the other hand, the hair cosmetic compositions of Comparative Examples 1 to 4 did not provide satisfactory results. For example, these compositions did not provide sufficient hair setting power and made the hair sticky under high-temperature and humidity conditions. Also, these compositions did not impart tautness and caused flaking. Furthermore, these compositions had insufficient antistatic properties.

<Test and Evaluation Methods—1>
(1) Hair Setting Power (Set Retention Power)

hung in a box maintained at 30° C. and 95% RH. After three hours, the loosening state of the hair is measured, and curl retention (%) is determined from the formula of curl retention.

$$\text{Curl Retention (\%)} = \frac{L - L_t}{L - L_0} \times 100$$

L: length of hair fully extended (23 cm)
$L_0$: length of hair before exposure
$L_t$: length of hair after exposure at time
A: having a curl retention of 71% or greater
B: having a curl retention of 40 to 70%
C: having a curl retention of 20% or greater but less than 40%
D: having a curl retention of less than 20%.

(2) Tautness of Hair

A curled hair bundle obtained in a manner similar to the above test for hair setting power (set retention) stored under thermo-hygrostatic conditions at 23° C. and 50% RH. The touch feeling such as tautness or resilience at the time when the curl is pressed by fingers is then evaluated.

A: having tautness and good resilience
B: having tautness but being fragile without resilience
C: having no tautness and inferior touch feeling (3) Stickiness Under High Humidity Conditions The curled hair bundle obtained in a manner similar to the above test for hair setting power (set retention) is stored under thermo-hygrostatic conditions at 30° C. and 90% RH. The touch feeling at the time when the curl is felt with fingers is then evaluated.

A: having no sticky feeling
B: having a slightly sticky feeling
C: having a sticky feeling (4) Flaking A bundle of smooth hairs having a length of 23 cm and a weight of 2 g is coated with a predetermined amount of each hair cosmetic composition using a dispenser or in the form of an aerosol. Immediately after coating, the bundle is smoothened by fingers to a strip form, followed by drying. The bundle is then stored under thermo-hygrostatic conditions at 23° C. and 60% RH, followed by combing. The amount of peeled polymer flakes present on the hair bundle is observed by a stereoscope (20 times).

A: no polymer flakes or a slight amount of polymer flakes is observed
B: polymer flakes are observed
C: a large amount of polymer flakes is observed (5) Antistatic properties (surface resistance)

A solution of the hair cosmetic composition having the composition shown in Table 1 is prepared. In the case where a propellant (dimethyl ether: DME, liquefied petroleum gas: LPG) is used, ethanol is added to the solution in the same amount as the propellant prior to filling.

The resulting solution is applied to a polypropylene film, which has been subjected to discharging treatment, using a 22-mil bar coater and then dried with a hair drier. The coated film is stored under thermo-hygrostatic conditions at 23° C. and 60%RH. The surface resistance is then measured with an insulation resistance tester ("HIGH MEGOHM METER", trade name; product of Takeda Riken Co.).

A: less than $1 \times 10^{10}$ Ω/□
B: $1 \times 10^{10}$ or greater but less than $1 \times 10^{12}$ Ω/□
C: $1 \times 10^{12}$ or greater Ω/□

Examples 7–10, Comparative Examples 5–8

Hair cosmetic compositions (water-containing aerosol or water-free aerosol) having the compositions shown in Table 2 were prepared in a manner well known to those of ordinary skill in the art and evaluated in a manner similar to Example 1. As seen from Table 2, the hair cosmetic compositions of Examples 7 to 10 exhibited excellent hair setting power, retained the shape of the curled hair even under high-temperature and humidity conditions, were free from sticking even under high-temperature and humidity conditions, imparted tautness and resilience, were free from flaking and had excellent antistatic properties.

On the other hand, the hair cosmetic compositions of Comparative Examples 5 to 8 did not provide satisfactory results. For example, these compositions provided insufficient hair setting power, caused sticking under high-temperature and humidity conditions, did not impart tautness, caused flaking or had insufficient antistatic properties.

Examples 11–13, Comparative Examples 9–11

Hair cosmetic compositions (in the form of a hair gel) having the compositions shown in Table 3 were prepared in a manner well known to those of ordinary skill in the art. The compositions were evaluated in a manner similar to Example 1, and also the gel condition (6) described below was evaluated.

<Test and Evaluation Method—2>

(6) Gel Condition

A gel obtained as described below is charged in a 50-ml clear glass bottle, followed by deaeration. The clearness of the liquid is visually observed. Then, the bottle is turned upside down and the fluidity of the gel solution in the bottle is observed.

A: solution is clear or almost clear and has almost no fluidity
B: solution is opaque or is fluid As seen from Table 3, any one of the compositions of the Examples and comparative Examples was good as a gel, having good transparency and good gel strength. It was also found that the hair cosmetic compositions obtained in Examples 11 to 13 exhibited excellent hair setting power, retained the shape of the curled hair even under high-temperature and humidity conditions, were free from sticking even under high-temperature and humidity conditions, imparted tautness and resilience, were free from flaking, and had excellent antistatic properties.

On the other hand, the hair cosmetic compositions of Comparative Examples 9 to 11 did not provide satisfactory results. For example, these compositions had insufficient hair setting power, caused sticking under high-temperature and humidity conditions, did not impart tautness, caused a flaking, or had insufficient antistatic properties.

TABLE 1

(%: in terms of effective components)

|  | Examples |  |  |  |  |  | Comparative Examples |  |  |  |
|---|---|---|---|---|---|---|---|---|---|---|
|  | 1 | 2 | 3 | 4 | 5 | 6 | 1 | 2 | 3 | 4 |
| P-1 | 2.5 | 2.0 | 0.5 | 3.0 | 2.0 | 2.0 | 3.0 | — | — | — |
| Nonionic resin 1 | 0.5 | 1.0 | 2.5 | 3.0 | — | — | — | 3.0 | — | — |
| Nonionic resin 2 | — | — | — | — | 1.0 | — | — | — | 3.0 | — |
| P-3 | — | — | — | — | — | 1.0 | — | — | — | 3.0 |
| Pure water | 45.0 | 45.0 | 45.0 | 45.0 | 45.0 | 45.0 | 45.0 | 45.0 | 45.0 | 60.0 |
| Ethanol | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 |
| Evaluation results |  |  |  |  |  |  |  |  |  |  |
| (1) Hair setting power | A | A | B | A | A | A | A | D | D | C |
| (2) Tautness of hair | A | A | A | A | A | A | C | B | B | B |
| (3) Stickiness at high humidity | A | A | A | A | A | A | A | C | C | C |
| (4) Flaking | A | A | A | A | A | A | A | C | C | C |
| (5) Antistatic properties | A | A | A | A | A | A | A | B | B | B |

TABLE 2

(%: in terms of effective components)

|  | Examples |  |  |  | Comparative Examples |  |  |  |
|---|---|---|---|---|---|---|---|---|
|  | 7 | 8 | 9 | 10 | 5 | 6 | 7 | 8 |
| P-1 | 2.0 | 2.0 | — | — | 3.0 | — | — | — |
| P-2 | — | — | 2.0 | 2.0 | — | 3.0 | — | — |
| Nonionic resin 1 | 1.0 | — | 1.0 | — | — | — | 3.0 | — |
| Nonionic resin 2 | — | 1.0 | — | 1.0 | — | — | — | 3.0 |
| Pure water | 20.0 | 20.0 | — | — | 20.0 | 20.0 | 20.0 | 20.0 |
| Ethanol | Balance | Balance | Balance | Balance | Balance | Balance | Balance | Balance |
| Stock | 60.0 | 60.0 | 70.0 | 70.0 | 60.0 | 60.0 | 60.0 | 60.0 |
| LPG | 10.0 | 10.0 | 30.0 | 30.0 | 10.0 | 10.0 | 10.0 | 10.0 |
| DME | 30.0 | 30.0 | — | — | 30.0 | 30.0 | 30.0 | 30.0 |
| Total | 100.0 | 100.0 | 100.0 | 100.0 | 100.0 | 100.0 | 100.0 | 100.0 |
| Evaluation results |  |  |  |  |  |  |  |  |
| (1) Hair setting power | A | A | A | A | A | A | D | D |
| (2) Tautness of hair | A | A | A | A | C | C | B | B |
| (3) Stickiness at high humidity | A | A | A | A | A | A | C | C |
| (4) Flaking | A | A | A | A | A | A | C | C |
| (5) Antistatic properties | A | A | A | A | A | A | B | B |

TABLE 3

(%: in terms of effective components)

|  | Examples |  |  | Comparative Examples |  |  |
|---|---|---|---|---|---|---|
|  | 11 | 12 | 13 | 9 | 10 | 11 |
| P-1 | 2.0 | 2.0 | 2.0 | 3.0 | — | — |
| Nonionic resin 1 | 1.0 | — | — | — | 3.0 | — |
| Nonionic resin 2 | — | 1.0 | — | — | — | — |
| P-3 | — | — | 1.0 | — | — | 3.0 |

TABLE 3-continued

| | Examples | | | Comparative Examples | | |
|---|---|---|---|---|---|---|
| | 11 | 12 | 13 | 9 | 10 | 11 |
| Neutralized product of carboxyvinyl polymer (*) | 0.5 | 0.5 | 0.5 | 0.5 | 0.5 | 0.5 |
| Pure water | Balance | Balance | Balance | Balance | Balance | Balance |
| Total | 100.0 | 100.0 | 100.0 | 100.0 | 100.0 | 100.0 |
| Evaulation results | | | | | | |
| (1) Hair setting power | A | A | A | A | C | C |
| (2) Tautness of hair | A | A | A | C | B | B |
| (3) Stickiness at high humidity | A | A | A | A | C | C |
| (4) Flaking | A | A | A | A | C | C |
| (5) Antistatic properties | A | A | A | A | B | B |
| (6) Condition of gel | A | A | A | A | A | A |

P-1: an amine-oxide-containing copolymer prepared in Preparation Example 1
P-2: an amine-oxide-containing copolymer prepared in Preparation Example 2
Nonionic resin 1: "Luviskol VA64" (trade name; product of BASF AG)
Nonionic resin 2: "Luviskol K90" (trade name; product of BASF AG)
P-3: an N-vinylformamide homopolymer as prepared in Preparation Example 3
(*) neutralized product of a carboxyvinyl polymer: 70 mole % of the acid portion of "Carbopol 940" (trade name; product of BF Goodrich) neutralized with 2-amino-2-methyl-1-propanol Examples 14–19, Comparative Examples 12–15

Hair cosmetic compositions (in the form of a hair spray pump) having the compositions shown in Table 4 were prepared in a manner well known to those of ordinary skill in the art. The hair setting power (set retention) when the hair was set with these compositions, the touch feeling such as resilience and stickiness under high humidity conditions, and the sliding feeling and combing property at the time of application, and smoothness of the hair after drying were evaluated.

As seen from Table 4, the compositions of Examples 14 to 19 exhibited have excellent hair setting power, retained the shape of the curled hair even under high-temperature and humidity conditions, imparted good resilience free of sticking even under high humidity conditions, provided a good touch feeling and combing property at the time of application, and provided a smooth touch feeling after drying.

On the other hand, the hair cosmetic compositions of Comparative Examples 12 to 15 did not provide satisfactory results. For example, these compositions provided insufficient hair setting power, caused the hair to stick under high humidity conditions and had insufficient resilience.

The test and evaluation methods other than those carried out in Example 1 are as follows:

(6) Resilience of Hair

A curled hair bundle obtained in a manner similar to the test of hair setting power (set retention) is stored under thermo-hygrostatic conditions at 25° C. and 80% RH, and the resilience of the hair at the time when the curl is pressed with fingers is then evaluated.

A: having good resilience
B: having resilience
C: having weak resilience (7) Stickiness of Hair The curled hair bundle obtained in a similar manner to the test of hair setting power (set retention) is stored under thermo-hygrostatic conditions at 25° C. and 80% RH, and the stickiness of the hair at the time when the curled hair is felt with fingers is then evaluated.

A: having no stickiness
B: having a slight stickiness
C: having substantial stickiness (8) Sliding feeling when the hair is wet A predetermined amount of each hair cosmetic composition prepared on an experimental base is applied to a bundle of smooth hairs having a length of 23 cm and a weight of 2 g. Immediately after application, the sliding feeling when the hair bundle is felt with fingers and combing ease are evaluated.

A: having sliding feeling and permitting easy combing
B: having insufficient sliding feeling and permitting slightly easy combing
C: having no sliding feeling and having difficulty in combing (9) Smoothness of Hair after Drying A predetermined amount of each hair cosmetic composition prepared on an experimental basis is applied to a bundle of smooth hairs having a length of 23 cm and a weight of 2 g, followed by drying with a drier. The dried hair bundle is stored under thermo-hygrostatic conditions at 23° C. and 60% RH and the smoothness when the hair bundle is felt with fingers is then evaluated.

A: having a smooth touch
B: having insufficient smoothness
C: having no smoothness and an interrupted touch Examples 20–23, Comparative Examples 16–19

Hair cosmetic compositions (in the form of a hair spray foam) having the compositions shown in Table 5 were prepared in a manner well known to those of ordinary skill in the art and evaluated in a manner similar to Example 14. As seen from Table 5, the compositions of Examples 20 to 23 exhibited excellent hair setting power, retained a curled hair shape even under high-temperature and humidity conditions, imparted the hair with good resilience free of stickiness even under high humidity conditions, had a good touch feeling and combing property at the time of application, and provided a smooth touch feeling after drying.

On the other hand, the hair cosmetic compositions of Comparative Examples 16 to 19 did not provide satisfactory results. For example, these compositions had insufficient hair setting power, imparted stickiness under high humidity conditions, and had insufficient resilience.

TABLE 4

| | Examples | | | | | | (%: in terms of effective components) Comparative Examples | | | |
|---|---|---|---|---|---|---|---|---|---|---|
| | 14 | 15 | 16 | 17 | 18 | 19 | 12 | 13 | 14 | 15 |
| P-1 | 2.5 | 2.0 | 0.5 | 2.0 | 2.0 | 3.0 | 3.0 | — | — | — |
| Cationic resin 1 | 0.5 | 1.0 | 2.5 | — | — | — | — | 3.0 | — | — |
| Cationic resin 2 | — | — | — | 1.0 | — | — | — | — | 3.0 | — |
| Cationic resin 3 | — | — | — | — | 1.0 | 3.0 | — | — | — | 3.0 |
| Pure water | 45.0 | 45.0 | 45.0 | 45.0 | 45.0 | 45.0 | 45.0 | 45.0 | 45.0 | 45.0 |
| Ethanol | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 |
| Evaluation results | | | | | | | | | | |
| (1) Hair setting power | A | A | A | A | A | A | A | B | C | C |
| (2) Resilience | A | A | A | A | A | A | A | B | C | C |
| (3) Stickiness | A | A | A | A | A | A | A | C | C | C |
| (4) Sliding feeling | A | A | A | A | A | A | C | A | A | A |
| (5) Smoothness | A | A | A | A | A | A | B | A | A | A |

TABLE 5

| | Examples | | | | (%: in terms of effective components) Comparative Examples | | | |
|---|---|---|---|---|---|---|---|---|
| | 20 | 21 | 22 | 23 | 16 | 17 | 18 | 19 |
| P-1 | 2.0 | — | — | — | — | — | — | — |
| P-2 | — | 2.0 | 2.0 | 2.0 | 3.0 | — | — | — |
| Cationic resin 1 | 1.0 | 1.0 | — | — | — | 3.0 | — | — |
| Cationic resin 2 (P-4) | — | — | 1.0 | — | — | — | 3.0 | — |
| Cationic resin 3 | — | — | — | 1.0 | — | — | — | 3.0 |
| Nonionic surfactant (*1) | 0.5 | 0.5 | 0.5 | 0.5 | 0.5 | 0.5 | 0.5 | 0.5 |
| Pure water | Balance | Balance | Balance | Balance | Balance | Balance | Balance | Balance |
| Stock | 92.5 | 92.5 | 92.5 | 92.5 | 92.5 | 92.5 | 92.5 | 92.5 |
| LPG | 7.5 | 7.5 | 7.5 | 7.5 | 7.5 | 7.5 | 7.5 | 7.5 |
| Total | 100.0 | 100.0 | 100.0 | 100.0 | 100.0 | 100.0 | 100.0 | 100.0 |
| Evaluation results | | | | | | | | |
| (1) Hair setting power | A | A | A | A | A | C | C | C |
| (2) Resilience | A | A | A | A | A | B | C | C |
| (3) Stickiness | A | A | A | A | A | C | C | C |
| (4) Sliding feeling | A | A | A | A | C | A | A | B |
| (5) Smoothness | A | A | A | A | B | A | A | A |

P-1: an amine-oxide-containing copolymer prepared in Preparation Example 1
P-2: an amine-oxide-containing copolymer prepared in Preparation Example 2
Cationic resin 1: "Ucare Polymer JR400" (trade name; product of Amerchol)
Cationic resin 2: a quaternary-ammonium-salt-containing acrylic resin (P-4) as prepared in Preparation Example 4
Cationic resin 3: "Gafquat 755N (trade name; product of ISP, Inc.)
(*1): polyoxyethylene (9 mole) lauryl ether ("NIKKOL BL9-EX", trade name; product of Nikko Chemicals)

Examples 24–29, Comparative Examples 20–23

Hair cosmetic compositions (pump spray) having the compositions shown in Table 6 were prepared in a manner well known to those of ordinary skill in the art. The hair setting power (set retention), hair tautness and flaking when setting the hair with these compositions, and the antistatic properties (surface resistance) thereof when applied to a polypropylene film were evaluated.

As seen from Table 6, the compositions of Examples 24 to 29 had excellent hair setting power, retained a curled hair shape even under high-temperature and humidity conditions, impart the hair with tautness and good resilience, was free from flaking, and had excellent antistatic properties.

On the other hand, the hair cosmetic compositions of Comparative Examples 20 to 23 did not provide satisfactory results. For example, these compositions had insufficient hair setting power, did not impart the hair with tautness, caused flaking, or had insufficient antistatic properties.

Examples 30–33, Comparative Examples 24–27

Hair cosmetic compositions (water-containing aerosol or water-free aerosol) having the compositions shown in Table 7 were prepared in a manner well known to those of ordinary skill in the art. As a result of the evaluation, as seen from Table 7, the compositions of Examples 30 to 33 exhibited excellent hair setting power, retained a curled hair shape even under high-temperature and humidity conditions, imparted the hair with tautness and good resilience, were free from flaking, and had excellent antistatic properties.

On the other hand, the hair cosmetic compositions of Comparative Examples 24 to 27 did not provide satisfactory results. For example, these compositions had insufficient hair setting power, did not impart the hair with tautness, caused a flaking, or had insufficient antistatic properties.

TABLE 6

(%: in terms of effective components)

|  | Examples | | | | | | Comparative Examples | | | |
| --- | --- | --- | --- | --- | --- | --- | --- | --- | --- | --- |
|  | 24 | 25 | 26 | 27 | 28 | 29 | 20 | 21 | 22 | 23 |
| P-1 | 2.5 | 2.0 | 0.5 | 3.0 | 2.0 | 2.0 | 3.0 | — | — | — |
| Anionic resin 1 | 0.5 | 1.0 | 2.5 | 3.0 | — | — | — | 3.0 | — | — |
| Anionic resin 2 | — | — | — | — | 1.0 | — | — | — | 3.0 | — |
| Anionic resin 3 | — | — | — | — | — | 1.0 | — | — | — | 3.0 |
| Pure water | 45.0 | 45.0 | 45.0 | 45.0 | 45.0 | 45.0 | 45.0 | 45.0 | 45.0 | 45.0 |
| Ethanol | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 |
| Evaluation results | | | | | | | | | | |
| (1) Hair setting power | A | A | A | A | A | A | A | B | C | C |
| (2) Tautness of hair | A | A | A | A | A | A | C | B | B | B |
| (3) Flaking | A | A | A | A | A | A | A | C | C | C |
| (4) Antistatic properties | A | A | A | A | A | A | A | C | C | C |

TABLE 7

(%: in terms of effective components)

|  | Examples | | | | Comparative Examples | | | |
| --- | --- | --- | --- | --- | --- | --- | --- | --- |
|  | 30 | 31 | 32 | 33 | 24 | 25 | 26 | 27 |
| P-1 | 2.0 | 2.0 | — | — | 3.0 | — | — | — |
| P-2 | — | — | 2.0 | 2.0 | — | 3.0 | — | — |
| Anionic resin 1 | 1.0 | — | 1.0 | — | — | — | 3.0 | — |
| Anionic resin 2 | — | 1.0 | — | 1.0 | — | — | — | 3.0 |
| Pure water | 20.0 | 20.0 | — | — | 20.0 | 20.0 | 20.0 | 20.0 |
| Ethanol | Balance | Balance | Balance | Balance | Balance | Balance | Balance | Balance |
| Stock | 60.0 | 60.0 | 70.0 | 70.0 | 60.0 | 60.0 | 60.0 | 60.0 |
| LPG | 10.0 | 10.0 | 30.0 | 30.0 | 10.0 | 10.0 | 10.0 | 10.0 |
| DME | 30.0 | 30.0 | | | 30.0 | 30.0 | 30.0 | 30.0 |
| Total (parts) | 100.0 | 100.0 | 100.0 | 100.0 | 100.0 | 100.0 | 100.0 | 100.0 |
| Evaluation results | | | | | | | | |
| (1) Hair setting power | A | A | A | A | A | A | C | C |
| (2) Tautness of hair | A | A | A | A | C | C | B | B |
| (3) Flaking | A | A | A | A | A | A | C | C |
| (4) Antistatic properties | A | A | A | A | A | A | C | C |

P-1: an amine-oxide-containing copolymer prepared in Preparation Example 1
P-2: an amine-oxide-containing copolymer prepared in Preparation Example 2
Anionic resin 1: "Diahold LP503" (trade name; "Mitsubishi Chemical)
Anionic resin 2: 20 mole % of the acid portion of "Gantletz ES-225" (trade name; product of ISP, Inc) neutralized with 2-amino-2-methyl-1-propanol
Anionic resin 3: 90 mole % of the acid portion of "Resin 28-2930", trade name; product of National Starch) neutralized with 2-amino-2-methyl-1-propanol Examples 34–40, Comparative Examples 28–32

Hair cosmetic compositions (pump spray) having the compositions shown in Table 8 were prepared in a manner well known to those of ordinary skill in the art. The hair setting power (set retention), tautness of the hair, flaking when setting the hair with the resulting hair cosmetic compositions, and washing removability were evaluated.

As seen from Table 8, the hair cosmetic compositions of Examples 34 to 40 exhibited excellent hair setting power, retained the shape of the curled hair even under high-temperature and humidity conditions, imparted the hair with tautness and resilience, were free from flaking, and had excellent washing removability.

On the other hand, the hair cosmetic compositions of Comparative Examples 28 to 32 did not provide satisfactory results. For example, these compositions did not provide sufficient hair setting power, did not impart the hair with tautness, caused flaking, or had insufficient washing removability.

Examples 41–44, Comparative Examples 33–36

Hair cosmetic compositions (water-containing aerosol, water-free aerosol) having the compositions shown in Table 9 were prepared in a manner well known to those of ordinary skill in the art, and were evaluated in a manner similar to Example 1. As seen from Table 9, the hair cosmetic compositions of Examples 41 to 44 exhibited excellent hair setting power, retained a curled hair shape even under high-temperature and humidity conditions, were free from flaking, and had excellent washing removability.

On the other hand, the hair cosmetic compositions of Comparative Examples 33 to 36 did not provide satisfactory results. For example, these compositions did not provide sufficient hair setting power, did not impart the hair with tautness, caused flaking, and had insufficient washing removability.

TABLE 8

(%: in terms of effective components)

|  | Examples | | | | | | | Comparative Examples | | | | |
| --- | --- | --- | --- | --- | --- | --- | --- | --- | --- | --- | --- | --- |
|  | 34 | 35 | 36 | 37 | 38 | 39 | 40 | 28 | 29 | 30 | 31 | 32 |
| P-1 | 2.5 | 2.0 | 0.5 | 3.0 | 2.0 | 2.0 | 2.0 | 3.0 | — | — | — | — |
| Amphoteric resin 1 | 0.5 | 1.0 | 2.5 | 3.0 | — | — | — | — | 3.0 | — | — | — |
| Amphoteric resin 2 | — | — | — | — | 1.0 | — | — | — | — | 3.0 | — | — |
| Amphoteric resin 3 | — | — | — | — | — | 1.0 | — | — | — | — | 3.0 | — |
| Amphoteric resin 4 | — | — | — | — | — | — | 1.0 | — | — | — | — | 3.0 |
| Pure water | 45.0 | 45.0 | 45.0 | 45.0 | 45.0 | 45.0 | 45.0 | 45.0 | 45.0 | 45.0 | 45.0 | 45.0 |
| Ethanol | Balance | Balance | Balance | Balance | Balance | Balance | Balance | Balance | Balance | Balance | Balance | Balance |
| Total (parts) | 100.0 | 100.0 | 100.0 | 100.0 | 100.0 | 100.0 | 100.0 | 100.0 | 100.0 | 100.0 | 100.0 | 100.0 |
| Evaluation results | | | | | | | | | | | | |
| (1) Hair setting power | A | A | B | A | A | A | B | A | B | B | C | D |
| (2) Tautness of hair | A | A | A | A | A | A | A | C | B | B | B | B |
| (3) Flaking | A | A | A | A | A | A | A | B | A | A | B | A |
| (4) Washing removability | A | A | A | A | A | A | A | A | C | C | A | A |

TABLE 9

(%: in terms of effective components)

|  | Examples | | | | Comparative Examples | | | |
| --- | --- | --- | --- | --- | --- | --- | --- | --- |
|  | 41 | 42 | 43 | 44 | 33 | 34 | 35 | 36 |
| P-1 | 2.0 | 2.0 | — | — | 3.0 | — | — | — |
| P-2 | — | — | 2.0 | 2.0 | — | 3.0 | — | — |
| Amphoteric resin 1 | 1.0 | — | 1.0 | — | — | — | 3.0 | — |

TABLE 9-continued

|  | Examples | | | | (%: in terms of effective components) Comparative Examples | | | |
| --- | --- | --- | --- | --- | --- | --- | --- | --- |
|  | 41 | 42 | 43 | 44 | 33 | 34 | 35 | 36 |
| Amphoteric resin 2 | — | 1.0 | — | 1.0 | — | — | — | 3.0 |
| Pure water | 20.0 | 20.0 | — | — | 20.0 | 20.0 | 20.0 | 20.0 |
| Ethanol | Balance | Balance | Balance | Balance | Balance | Balance | Balance | Balance |
| Stock | 60.0 | 60.0 | 70.0 | 70.0 | 60.0 | 60.0 | 60.0 | 60.0 |
| LPG | 10.0 | 10.0 | 30.0 | 30.0 | 10.0 | 10.0 | 10.0 | 10.0 |
| DME | 30.0 | 30.0 | — | — | 30.0 | 30.0 | 30.0 | 30.0 |
| Total | 100.0 | 100.0 | 100.0 | 100.0 | 100.0 | 100.0 | 100.0 | 100.0 |
| Evaulation results |  |  |  |  |  |  |  |  |
| (1) Hair setting power | A | A | A | A | A | A | B | C |
| (2) Tautness of hair | A | A | A | A | C | C | B | B |
| (3) Flaking | A | A | A | A | B | B | A | A |
| (4) Washing removability | A | A | A | A | A | A | C | A |

P-1: Amine-oxide-containing copolymer prepared in Preparation Example 1
P-2: Amine-oxide-containing copolymer prepared in Preparation Example 2
Amphoteric resin 1: "Yukaformer AMPHOSET" (trade name; product of Mitsubishi Chemical)
Amphoteric resin 2: "Yukaformer SM" (trade name; product of Mitsubishi Chemical)
Amphoteric resin 3: "Amformer 28-4910" (trade name; product of National Starch); 100% of the acid equivalent was neutralized with 2-amino-2-methyl-1-propanol
Amphoteric resin 4: "Merquat Plus 3330" (trade name; product of Calgon)
DME: dimethyl ether
LPG: liquefied petroleum gas <Water Solubility>

One part by weight of a polymer and 99 parts by weight of deionized water are stirred under heat at 60° C. for 2 hours. The aqueous solution thus obtained was stored for one day after cooling and its transmittance at a wavelength of 655 nm in a 1 cm×1 cm cell is measured. The water solubility was ranked as A, B and when the transmittance are 70 to 100%, 30 to 70% and 0 to 30%, respectively.

All polymers, amine-oxide-containing polymers P1 to P4, nonionic resins 1 and 2, cationic resins 1 to 3, anionic resins 1 to 3 and amphoteric resin 1 to 4 were on the rank A.

While the invention has been described in detail and with reference to specific examples thereof, it will be apparent to one skilled in the art that various changes and modifications can be made therein without departing from the spirit and scope thereof.

What is claimed is:

1. A hair cosmetic composition comprising:
   (a) a water-soluble amine-oxide-containing polymer having a weight-average molecular weight of 10,000 to 500,000, obtained by polymerizing
      (A) 15 to 90 wt. % of an amine-oxide containing monomer, and
      (B) 10–85 wt. % of a hydrophobic unsaturated monomer, and
   (b) a water-soluble polymer selected from the group consisting of nonionic polymers, cationic polymers, anionic polymers and amphoteric polymers, the weight ratio of said component (a) to said component (b) being within a range of from 1:10 to 10:1, and said components (a) and (b) being present in a total amount of 0.1 to 10 wt. % based on the hair cosmetic composition.

2. The hair cosmetic composition according to claim 1, wherein the amine-oxide-containing monomer (A) is selected from compounds represented by the following formulas (I) to (IV):

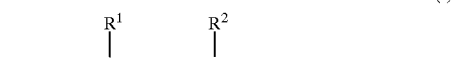

(I)

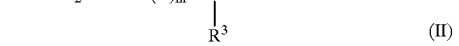

(II)

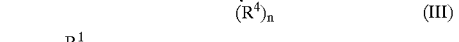

(III)

(IV)

wherein $R^1$ represents a hydrogen atom or a methyl group, $R^2$ and $R^3$ are the same or different and each independently represents a $C_{1-24}$ alkyl group, a $C_{6-24}$ aryl group or a $C_{7-24}$ arylalkyl group, $R^4$ and $R^5$ each independently represents a $C_{1-24}$ alkyl group, a $C_{6-24}$ aryl group or a $C_{7-24}$ arylalkyl group, X represents a divalent linking group, m is 0 or 1, n is an integer of 0 to 4 and p is an integer of 0 to 3, Y represents

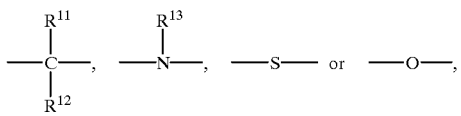

at least one of $R^6$ to $R^{13}$ represents

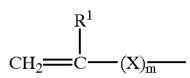

and the other of $R_6$ to $R_{13}$ each represents a hydrogen atom or a $C_{1-24}$ alkyl group, a $C_{6-24}$ aryl group or a $C_{7-24}$ arylalkyl group, and a and b are the same or different and each independently represents an integer of 1 to 10.

3. The hair cosmetic composition according to claim 1, wherein the hydrophobic unsaturated monomer (B) is a compound represented by the following formula (V):

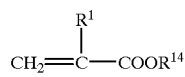

(V)

wherein $R^1$ represents a hydrogen atom or a methyl group and $R^{14}$ represents a $C_{1-24}$ alkyl group.

4. The hair cosmetic composition according to claim 1, wherein said component (b) comprises a nonionic polymer having a repeating unit derived from an unsaturated monomer containing a moiety selected from the group consisting of a pyrrolidone ring, a caprolactam ring, an amide group, an N-alkyl-substituted amide group, a polyether group, a formamide group and an acetamide group.

5. The hair cosmetic composition according to claim 1, wherein said component (b) comprises a cationic polymer which is at least one macromolecule selected from the group consisting of the following compounds:

(1) a cationic polymer which is a polymer or copolymer of at least one of N-vinylpyrrolidone and N-vinylcaprolactam;

(2) a cationic polymer which is a polymer or copolymer of dimethyldiallyl ammonium;

(3) a cationic polymer which is a polymer or copolymer of at least one of an acrylic ester of a quaternary ammonium salt and a methacrylic ester of a quaternary ammonium salt; and (4) a cationic polymer of a quaternary ammonium salt of a cellulose or chitosan compound.

6. The hair cosmetic composition according to claim 1, wherein said component (b) comprises a carboxyl-containing or sulfonic-acid-containing anionic polymer.

7. The hair cosmetic composition according to claim 1, wherein said component (b) comprises an amphoteric polymer having a repeating unit derived from an unsaturated monomer containing a betaine group.

8. The hair cosmetic composition according to claim 1, wherein said component (b) comprises an amphoteric polymer having a repeating unit derived from an unsaturated monomer containing an anionic group and a repeating unit derived from an unsaturated monomer containing a group having a quaternary ammonium salt or a tertiary amino group.

9. The hair cosmetic composition according to claim 1, wherein said component (b) comprises a water-soluble polymer having a weight-average molecular weight of from 5,000 to 500,000.

10. A hair mousse injectable in a foam form, which comprises:

(a) 0.1 to 9 wt. % of a water-soluble amine-oxide-containing polymer having a weight-average molecular weight of 10,000 to 500,000, (b) 0.1 to 9 wt. % of a water-soluble polymer selected from the group consisting of nonionic polymers, cationic polymers, anionic polymers and amphoteric polymers, (c) 0.1 to 5 wt. % of a nonionic surfactant, (d) 3 to 25 wt. % of a liquefied gas, and (e) at least 60 wt. % of a water-soluble solvent.

11. The hair mousse according to claim 10, wherein said component (c) comprises a water-soluble solvent selected from the group consisting of water, ethanol and isopropanol.

12. The hair spray comprising:

(a) 0.1 to 9 wt. % of a water-soluble amine-oxide-containing polymer having a weight-average molecular weight of 10,000 to 500,000, (b) 0.1 to 9 wt. % of a water-soluble polymer selected from the group consisting of nonionic polymers, cationic polymers, anionic polymers and amphoteric polymers, (f) 30 to 80 wt. % of an organic solvent having a boiling point of 50 to 300° C., and (g) 10 to 60 wt. % of a propellant.

13. The hair spray according to claim 12, wherein said component (f) comprises an organic solvent selected from the group consisting of ethanol, isopropyl alcohol and ethylene glycol.

14. The hair spray according to claim 12, wherein said propellant is selected from the group consisting of trichloromonofluoromethane, dichlorodifluoromethane, liquefied petroleum gas, dimethyl ether, halogenated hydrocarbon, compressed air, compressed carbon dioxide gas and compressed nitrogen gas.

15. A hair gel comprising:

(a) 0.1 to 9 wt. % of a water-soluble amine-oxide-containing polymer having a weight-average molecular weight of 10,000 to 500,000, (b) 0.1 to 9 wt. % of a water-soluble polymer selected from the group consisting of nonionic polymers, cationic polymers, anionic polymers and amphoteric polymers, (h) 0.1 to 3 wt. % of a gel base, and (i) at least 72 wt. % of water.

16. The hair gel according to claim 15, wherein the gel base (h) comprises a basic compound of a carboxyvinyl polymer.

17. A hair setting lotion comprising:

(a) 0.1 to 9 wt. % of a water-soluble amine-oxide-containing polymer having a weight-average molecular weight of 10,000 to 500,000, (b) 0.1 to 9 wt. % of a water-soluble polymer selected from the group consisting of nonionic polymers, cationic polymers, anionic polymers and amphoteric polymers, and (j) a water soluble solvent in an amount of from 50 to 90 wt. %.

18. The hair cosmetic composition according to claim 1, wherein the hydrophobic unsaturated monomer is selected from the group consisting of $C_{1-24}$ alkyl (meth)acrylates, styrene, p-methylstyrene, p-chlorostyrene, vinyl methyl ether, vinyl cyclohexyl ether, vinyl acetate, diethyl maleate, dibutyl maleate, glycidyl (meth)acrylate and fluoroalkyl esters of (meth)acrylic acid and radical-polymerizable unsaturated-group-containing silicone macromonomers.

* * * * *